United States Patent
Ogilvie et al.

(10) Patent No.: US 7,338,490 B2
(45) Date of Patent: Mar. 4, 2008

(54) REDUCTION CABLE AND BONE ANCHOR

(75) Inventors: James Ogilvie, Edna, MN (US); Matthew M. Morrison, Cordova, TN (US); Michael S. Veldman, Olive Branch, MI (US); Harold S. Taylor, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 298 days.

(21) Appl. No.: 10/442,821

(22) Filed: May 21, 2003

(65) Prior Publication Data
US 2004/0111091 A1 Jun. 10, 2004

Related U.S. Application Data

(60) Provisional application No. 60/382,320, filed on May 22, 2002, provisional application No. 60/382,332, filed on May 21, 2002.

(51) Int. Cl.
*A61B 17/70* (2006.01)

(52) U.S. Cl. .......................................................... 606/61

(58) Field of Classification Search .................. 606/61, 606/59, 62, 63, 64, 69, 71–74, 86, 103, 105
See application file for complete search history.

(56) References Cited

U.S. PATENT DOCUMENTS

| 2,509,272 | A | 5/1950 | Karnuth et al. |
|---|---|---|---|
| 2,574,579 | A | 11/1951 | McCoy et al. |
| 4,271,836 | A | 6/1981 | Bacal et al. |
| 4,369,770 | A | 1/1983 | Bacal et al. |
| 4,404,967 | A | 9/1983 | Bacal et al. |
| 4,567,884 | A | 2/1986 | Edwards |
| 4,790,303 | A | 12/1988 | Steffee |
| 4,805,602 | A | 2/1989 | Puno et al. |
| 4,887,595 | A | 12/1989 | Heinig et al. |
| 4,889,110 | A | 12/1989 | Galline et al. |
| 5,000,165 | A | 3/1991 | Watanabe |
| 5,005,562 | A | 4/1991 | Cotrel |
| 5,007,909 | A * | 4/1991 | Rogozinski .................. 606/61 |
| 5,092,868 | A | 3/1992 | Mehdian |
| 5,242,446 | A | 9/1993 | Steffee et al. |
| 5,250,049 | A * | 10/1993 | Michael ....................... 606/72 |
| 5,267,999 | A | 12/1993 | Olerud |
| 5,304,178 | A | 4/1994 | Stahurski |
| 5,312,410 | A | 5/1994 | Miller et al. |
| 5,330,472 | A | 7/1994 | Metz-Stavenhagen |
| 5,374,267 | A | 12/1994 | Siegal |
| 5,395,374 | A | 3/1995 | Miller et al. |

(Continued)

FOREIGN PATENT DOCUMENTS

DE     3121271 C2     5/1989

(Continued)

*Primary Examiner*—Eduardo C. Robert
*Assistant Examiner*—David Comstock
(74) *Attorney, Agent, or Firm*—Woodard, Emhardt, Moriarty, McNett & Henry LLP

(57) ABSTRACT

Methods and apparatus for alignment of vertebrae. In one embodiment, the invention includes a hook-shaped member which receives a bone anchor, both the member and the anchor being fixed to a portion of bone. The assembly of hook and anchor are coupled to a surgical rod by a cable and connector.

38 Claims, 16 Drawing Sheets

U.S. PATENT DOCUMENTS

| | | |
|---|---|---|
| 5,415,658 A | 5/1995 | Kilpela et al. |
| 5,417,690 A | 5/1995 | Sennett et al. |
| 5,437,671 A | 8/1995 | Lozier et al. |
| 5,487,742 A | 1/1996 | Cotrel |
| 5,569,253 A | 10/1996 | Farris et al. |
| 5,584,832 A | 12/1996 | Schlapfer |
| 5,591,235 A | 1/1997 | Kuslich |
| 5,643,262 A | 7/1997 | Metz-Stavenhagen et al. |
| 5,651,789 A | 7/1997 | Cotrel |
| 5,702,399 A | 12/1997 | Kilpela et al. |
| 5,782,831 A | 7/1998 | Sherman et al. |
| 5,810,816 A | 9/1998 | Roussouly et al. |
| 5,810,818 A | 9/1998 | Errico et al. |
| 5,928,232 A | 7/1999 | Howland et al. |
| 5,935,133 A | 8/1999 | Wagner et al. |
| 5,964,769 A | 10/1999 | Wagner et al. |
| 6,004,327 A | 12/1999 | Asnis et al. |
| 6,053,921 A | 4/2000 | Wagner et al. |
| 6,063,090 A | 5/2000 | Schlapfer |
| 6,086,590 A | 7/2000 | Margulies et al. |
| 6,123,707 A | 9/2000 | Wagner |
| 6,132,464 A | 10/2000 | Martin |
| 6,187,005 B1 | 2/2001 | Brace et al. |
| 6,248,105 B1 | 6/2001 | Schlapfer et al. |
| 6,248,107 B1 | 6/2001 | Foley et al. |
| 6,251,111 B1 | 6/2001 | Barker et al. |
| 6,277,120 B1 | 8/2001 | Lawson |
| 6,299,613 B1 | 10/2001 | Ogilvie et al. |
| RE37,479 E | 12/2001 | Kuslich |
| 6,325,802 B1 | 12/2001 | Frigg |
| 6,371,957 B1 | 4/2002 | Amrein et al. |
| 6,391,030 B1 | 5/2002 | Wagner et al. |
| 6,423,065 B2 | 7/2002 | Ferree |
| 6,436,099 B1 | 8/2002 | Drewry et al. |
| 6,468,309 B1 | 10/2002 | Lieberman |
| 6,488,683 B2 | 12/2002 | Lieberman |
| 6,514,255 B1 | 2/2003 | Ferree |
| 6,524,315 B1 | 2/2003 | Selvitelli et al. |
| 6,527,774 B2 | 3/2003 | Lieberman |
| 6,544,265 B2 | 4/2003 | Lieberman |
| 6,547,790 B2 | 4/2003 | Harkey, III et al. |
| 6,551,319 B2 | 4/2003 | Lieberman |
| 6,551,320 B2 | 4/2003 | Lieberman |
| 6,558,389 B2 | 5/2003 | Clark et al. |
| 6,576,018 B1 | 6/2003 | Holt |
| 6,589,243 B1 | 7/2003 | Viart et al. |
| 6,605,091 B1 | 8/2003 | Iwanski |
| 6,638,279 B2 | 10/2003 | Bonutti |
| 6,645,211 B2 | 11/2003 | Magana |
| 6,648,903 B1 | 11/2003 | Pierson, III |
| 6,660,010 B2 | 12/2003 | Gellman |
| 2001/0005475 A1 | 6/2001 | Frigg |
| 2001/0027319 A1 | 10/2001 | Ferree |
| 2001/0034522 A1 | 10/2001 | Frigg |
| 2001/0053912 A1 | 12/2001 | Frigg |
| 2002/0032483 A1 | 3/2002 | Nicholson et al. |
| 2002/0045901 A1 | 4/2002 | Wagner et al. |
| 2002/0049446 A1 | 4/2002 | Harkey, III et al. |
| 2002/0055737 A1 | 5/2002 | Lieberman |
| 2002/0055738 A1 | 5/2002 | Lieberman |
| 2002/0055739 A1 | 5/2002 | Lieberman |
| 2002/0055740 A1 | 5/2002 | Lieberman |
| 2002/0055742 A1 | 5/2002 | Lieberman |
| 2002/0058940 A1 | 5/2002 | Frigg et al. |
| 2002/0072753 A1 | 6/2002 | Cohen |
| 2002/0099309 A1 | 7/2002 | Beger et al. |
| 2002/0107524 A1 | 8/2002 | Magana |
| 2002/0133155 A1 | 9/2002 | Ferree |
| 2002/0151903 A1 | 10/2002 | Takei et al. |
| 2002/0156484 A1 | 10/2002 | McKernan et al. |
| 2002/0156490 A1 | 10/2002 | Enayati |
| 2002/0161370 A1 | 10/2002 | Frigg et al. |
| 2002/0183847 A1 | 12/2002 | Lieberman |
| 2002/0188297 A1 | 12/2002 | Dakin et al. |
| 2003/0004519 A1 | 1/2003 | Torode et al. |
| 2003/0013936 A1 | 1/2003 | Jackson, III. |
| 2003/0014116 A1 | 1/2003 | Ralph et al. |
| 2003/0023241 A1 | 1/2003 | Drewry et al. |
| 2003/0036758 A1 | 2/2003 | Frigg et al. |
| 2003/0050644 A1 | 3/2003 | Boucher et al. |
| 2003/0069643 A1 | 4/2003 | Ralph et al. |
| 2003/0074021 A1 | 4/2003 | Morriss et al. |
| 2003/0078579 A1 | 4/2003 | Ferree |
| 2003/0078581 A1 | 4/2003 | Frei et al. |
| 2003/0078584 A1 | 4/2003 | Tipirneni |
| 2003/0105459 A1 | 6/2003 | Songer |
| 2003/0149432 A1 | 8/2003 | Frigg et al. |
| 2003/0181913 A1 | 9/2003 | Lieberman |
| 2003/0199877 A1 | 10/2003 | Steiger et al. |

FOREIGN PATENT DOCUMENTS

| | | |
|---|---|---|
| FR | 2 289 164 | 5/1976 |
| FR | 2 642 642 A1 | 8/1990 |
| WO | WO 94/17746 | 8/1994 |
| WO | WO 95/03002 | 2/1995 |

* cited by examiner

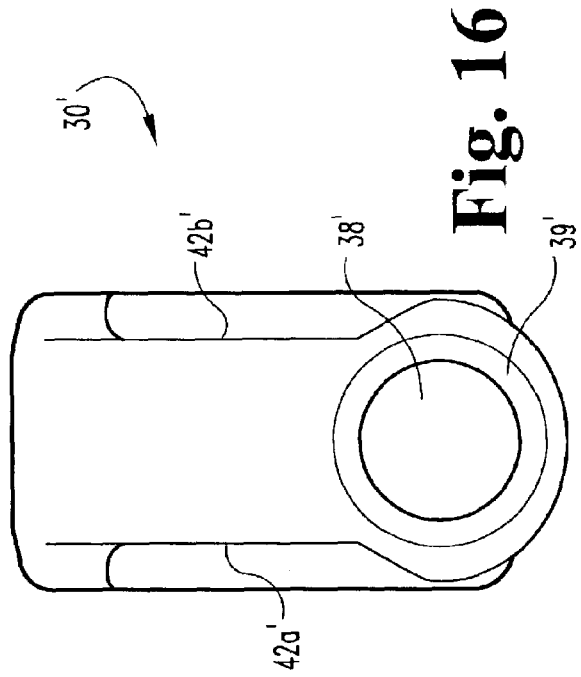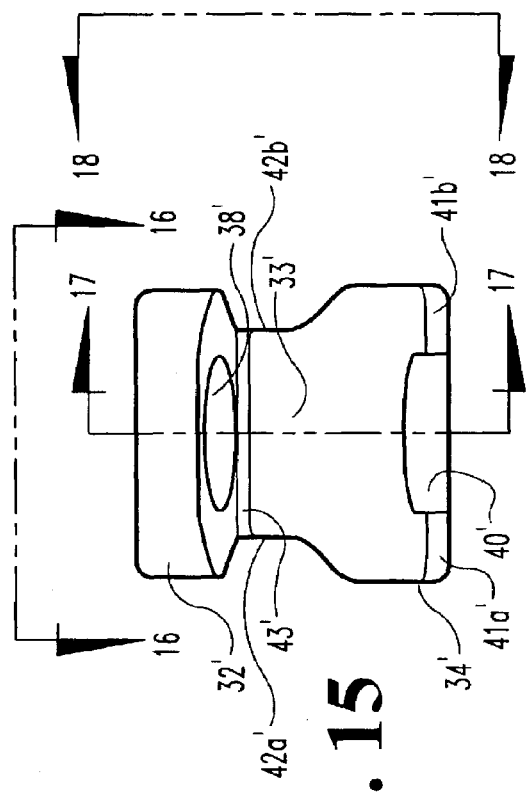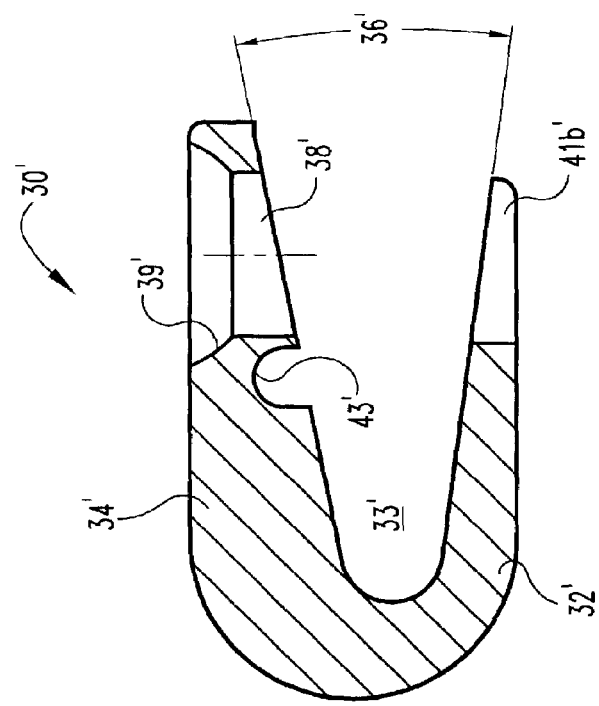

REDUCTION CABLE AND BONE ANCHOR

This application claims the benefit of priority to U.S. provisional patent application Ser. No. 60/382,332, filed May 21, 2002 and U.S. provisional patent application Ser. No. 60/382,320, filed May 22, 2002, both of which are incorporated herein by reference.

FIELD OF THE INVENTION

The present invention pertains to methods and apparatus for alignment of vertebrae.

BACKGROUND OF THE INVENTION

In some alignment surgeries, stainless steel wires are passed under the lamina, through the spinal canal, and tightened around spinal rods in a segmental manner. The wires are attached to rods progressively and segmentally in a method which reduces the distance between the curved spine and the contoured spinal rod.

Although this method is mostly effective, the passage of wires into the spinal canal has been reported as a source of clinical complications, both intra-operatively and post-operatively.

What is needed are methods and apparatus which permit attachment of vertebrae to a spinal rod without passing wires into the spinal canal. The present invention provides these methods and apparatus in novel and unobvious ways.

SUMMARY OF THE INVENTION

One embodiment of the present invention concerns an apparatus for alignment of vertebrae. The embodiment comprises a surgical rod and a hook-shaped member adapted and configured for receiving a portion of bone within the hook. The embodiment further includes an anchor having a body adapted and configured for fixation into a bone and a head, the anchor coupling to the member. The embodiment further includes a cable coupling said hook-shaped member to the rod.

Another embodiment of the present invention concerns an apparatus for alignment of vertebrae. The embodiment comprises a surgical rod and a hook-shaped member adapted and configured for receiving a portion of bone within the hook. The embodiment further includes a cable coupling the hook-shaped member to the rod and having first and second ends. The embodiment further includes a connecting member which receives therein the first end and the second end, each first and second ends being adapted and configured for pivotal coupling to the connecting member.

Yet another embodiment of the present invention concerns an apparatus for alignment of vertebrae. The embodiment comprises a surgical rod having a first cross-sectional shape. The embodiment further includes an anchor adapted and configured for fixation into a bone. The embodiment further includes a cable coupling the anchor to the rod and having first and second ends, and further includes a connecting member having a first extended portion connected to the first end of the cable and a second extended portion connected to the second end of the cable, and having a middle section between the first and second extended portions, the middle section having a second cross-sectional shape generally complementary to the cross-sectional shape of the rod.

A further embodiment of the present invention concerns an apparatus for alignment of vertebrae. The embodiment comprises a surgical rod and a hook-shaped member including first and second arms, one of the arms defining an open slot. The embodiment includes a bone anchor coupling the hook-shaped member to a bone. The embodiment includes a cable coupling the hook-shaped member to the rod, a portion of the cable being received within the open slot. The embodiment further includes a connecting member having a first extended portion connected to the cable and a second extended portion connected to the cable.

These and other objects of the present invention will be shown in the description of the preferred embodiment, the drawings and the claims to follow.

DESCRIPTION OF THE DRAWINGS

FIG. 15 is an end elevational view of an apparatus according an alternate embodiment of the present invention.

FIG. 16 is a view of the apparatus of FIG. 15 as taken along line 16-16 of FIG. 15.

FIG. 17 is a cross sectional view of the apparatus of FIG. 15 as taken along line 17-17 of FIG. 15.

DESCRIPTION OF THE PREFERRED EMBODIMENT

Figure 1:
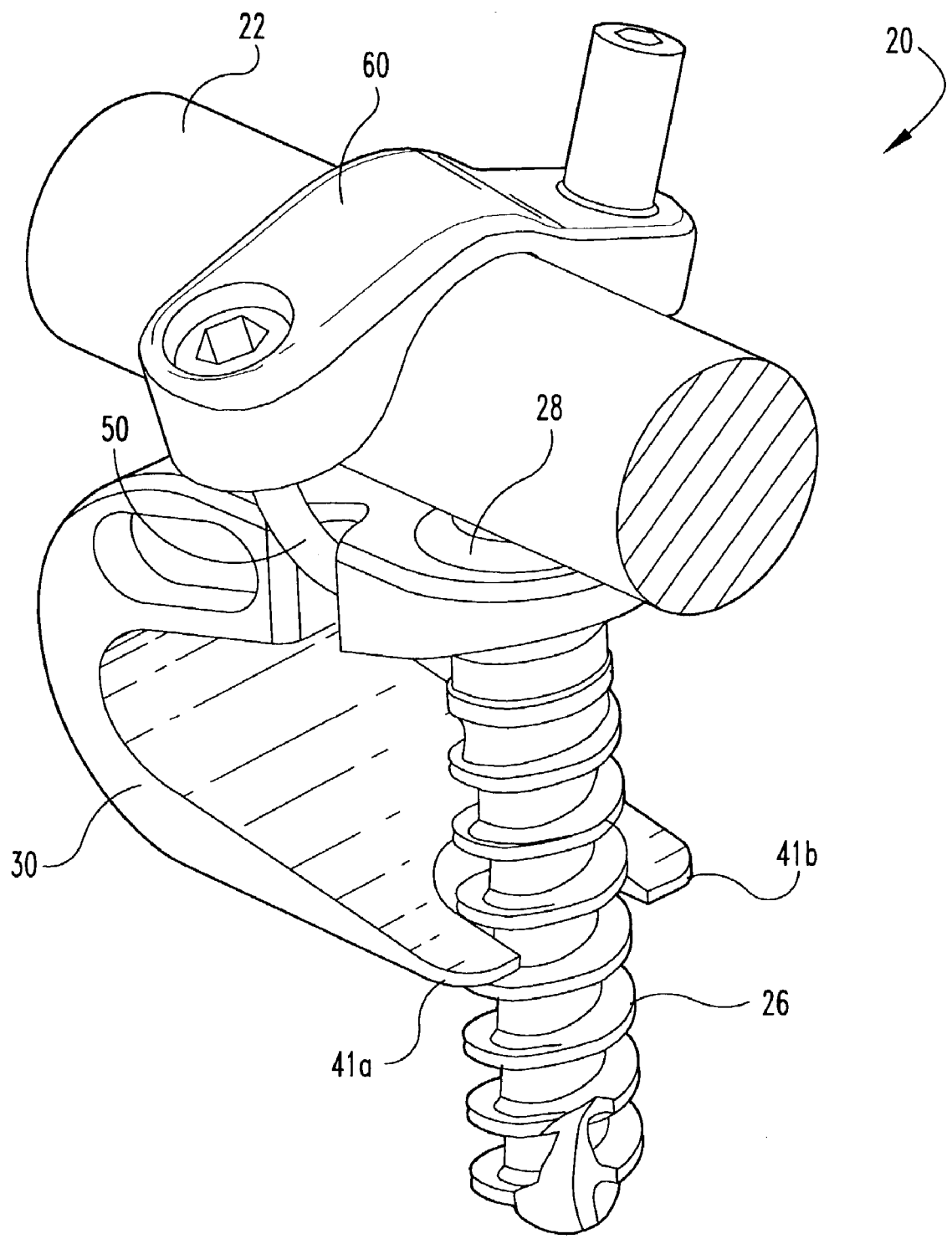
FIG. 1 is a perspective view of a cable and bone anchor assembly according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention relates to various apparatus and methods for alignment of vertebrae. In one embodiment, the invention includes a bone screw anchor including a swivel mechanism and a hook to provide a distributed load surface during reduction maneuvers. In some embodiments the hook is coupled to the vertebrae by a bone screw or a staple. In yet other embodiments the hook is maintained in a load-bearing orientation relative to the vertebrae by the relative placement of the hook, rod, and attaching cable. In these other embodiments, the bone screw, staple, or other fastening feature is optional. In yet other embodiments of the present invention, the hook is optional. In these embodiments, the bone screw, staple, or other fastener includes a passageway to accept the flexible cable placed therethrough. The cable directly connects the fastener to the connector without the need for the hook.

Figure 2:
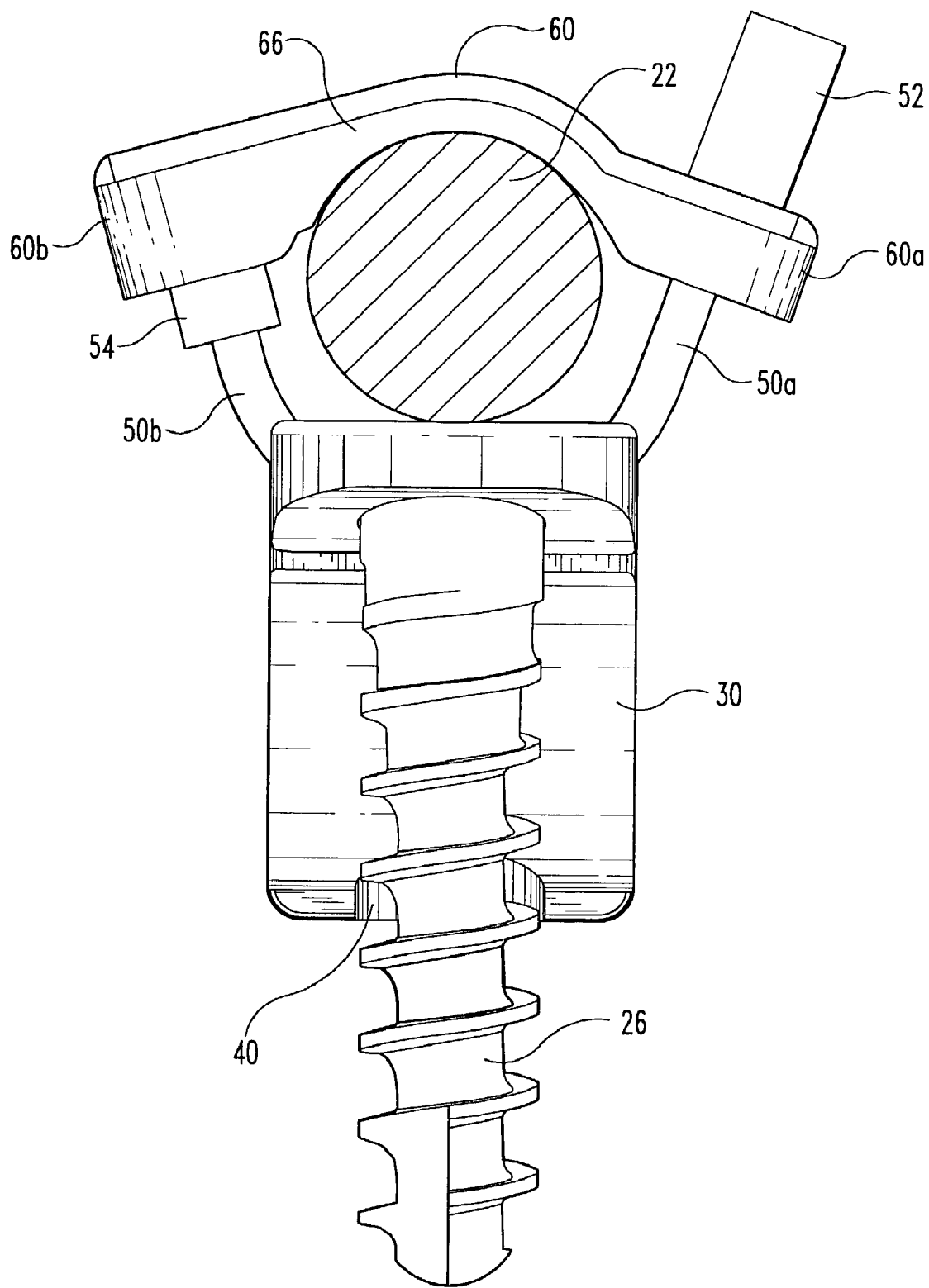
FIG. 2 is an elevational view of the assembly of FIG. 1.

Referring to FIGS. 1 and 2, an apparatus 20 is shown according to one embodiment of the present invention. A surgical rod 22 (shown in section) follows a path chosen by a surgeon and substantially parallel to the spine. Apparatus 20 includes a bone screw 26 which is anchored into a vertebrae (not shown). Screw 26 is rotatably coupled at one end to a hook-shaped member 30 which is adapted and configured for receiving a portion of bone within the hook. A section of flexible cable 50 passes around one arm of member 30 and couples member 30 to rod 22. The ends of cable 50 are coupled to a connector 60 which preferably straddles a portion of rod 22. With appropriate tightening of cable 50, member 30 and bone screw 26 apply a load into the vertebrae sufficient to position the vertebrae proximate to rod 22.

The extent to which cable 50 is tightened depends upon decisions by the surgeon. For example, in some embodiments of the present invention, there is a gap between rod 22 and hook 30, in contrast to the rod to hook contact depicted in FIG. 1. In these alternate embodiments, the surgeon can opt to provide limited tightening of cable 50 around rod 22. This limited tightening can take into account, for example, a decision on the part of the surgeon to move the selected vertebrae by a limited amount. Thus, the present invention contemplates embodiments in which cable 50 is tightened sufficiently to bring rod 22 snugly against a surface of hook 30 (which, in some embodiments of the present invention, causes the rod to cover at least a portion of the head), and also those embodiments in which a gap is maintained between rod 22 and surfaces of hook 30.

Figure 3:
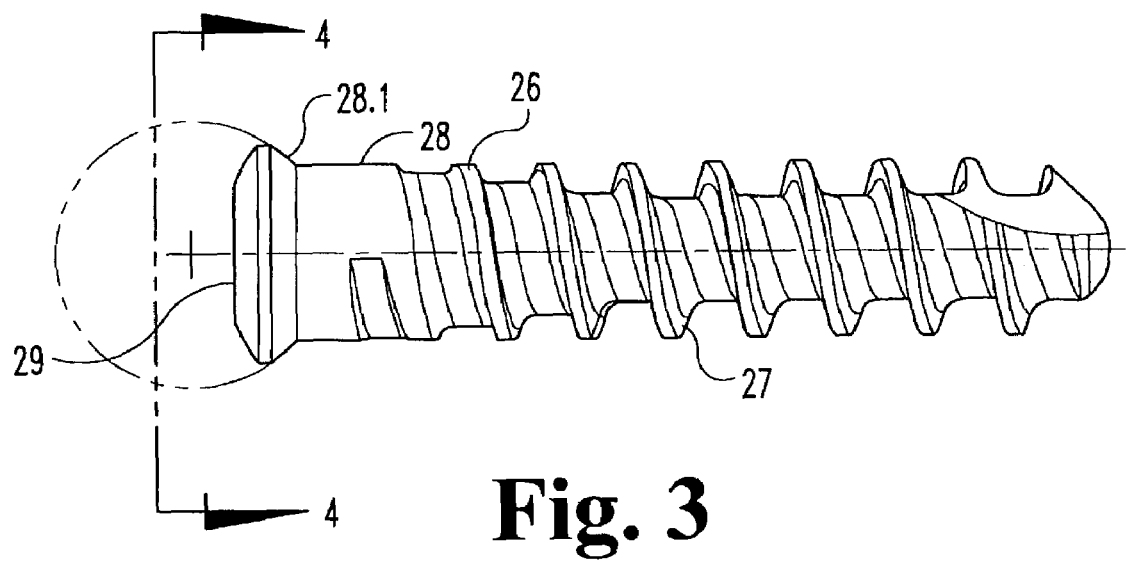
FIG. 3 is a side view of the bone screw of FIG. 1.
Figure 4:
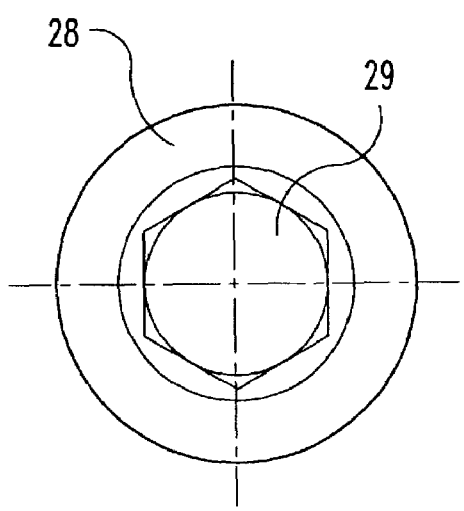
FIG. 4 is view of the apparatus of FIG. 3 as taken along line 4-4 of FIG. 3.

FIGS. 3 and 4 show side and end views, respectively, of bone screw 26. Screw 26 preferably includes self-tapping features and also features that resist undesirable loosening after implantation. Screw 26 includes a threaded shank 27 and a head 28. Head 28 preferably includes a semi-spherical surface 28.1 which rotatably couples screw 26 to one arm of member 30, as will be described later. Head 28 preferably includes a hex-shaped slot 29 for torquing of screw 26.

Figure 6:
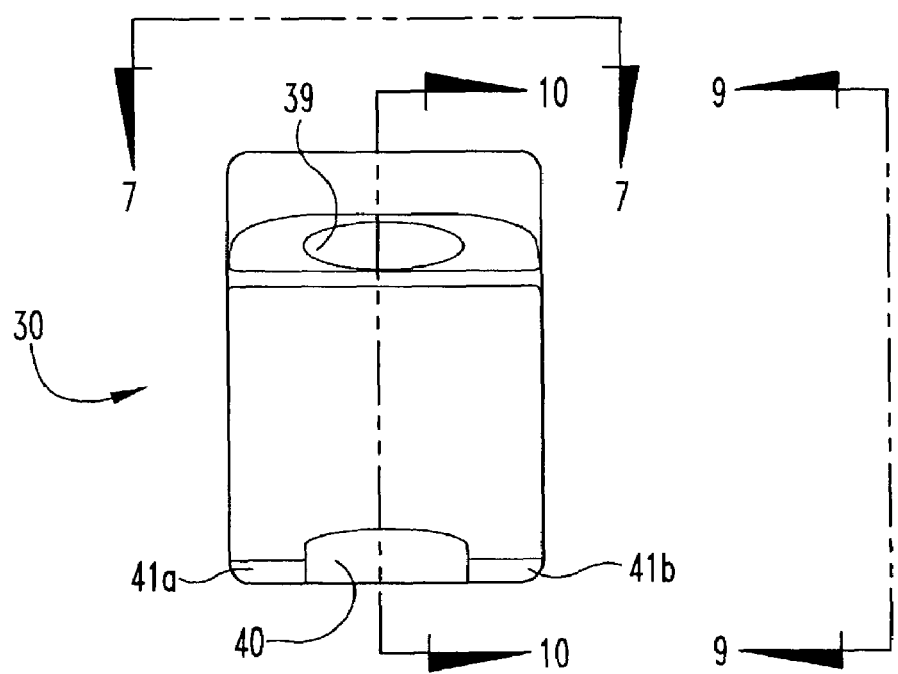
FIG. 6 is an end elevational view of the hook of the assembly of FIG. 1.
Figure 7:
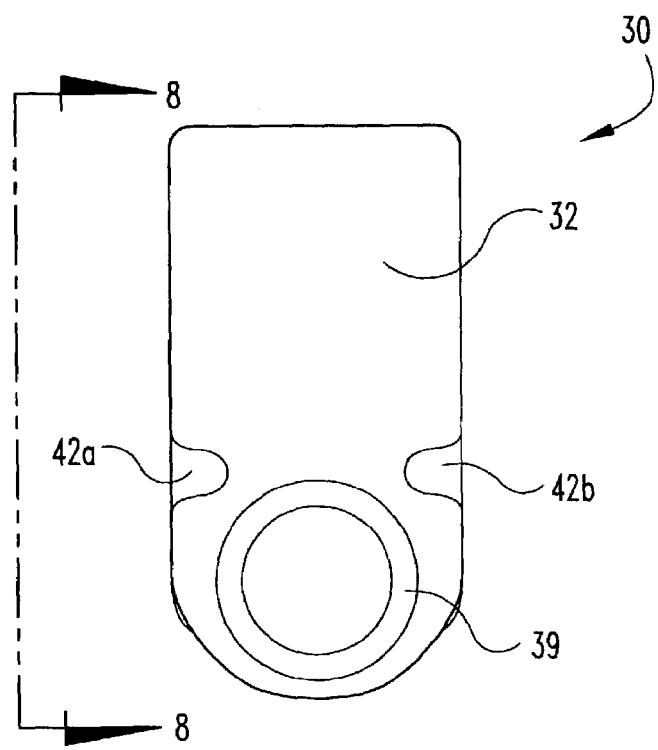
FIG. 7 is a top view of the apparatus of FIG. 6 as taken along line 7-7 of FIG. 6.
Figure 8:
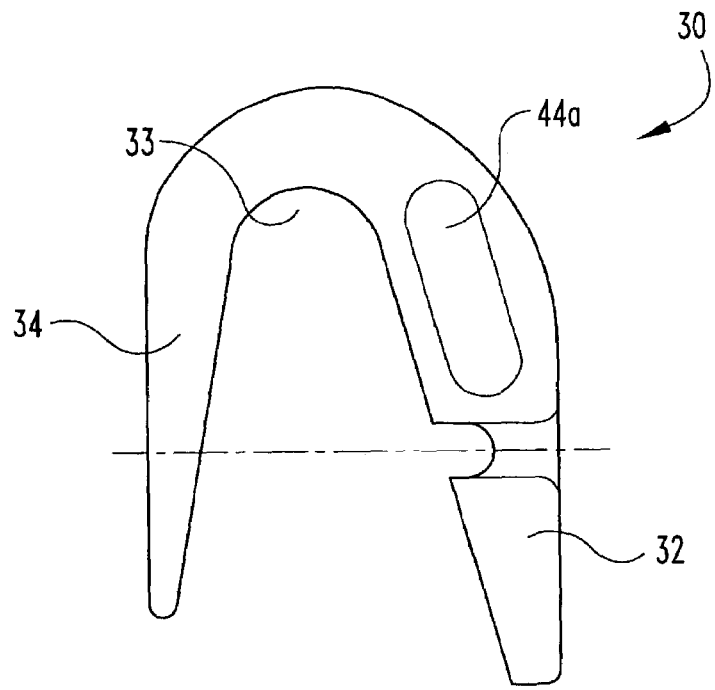
FIG. 8 is side elevational view of the apparatus of FIG. 7 as taken along line 8-8 of FIG. 7.
Figure 9:
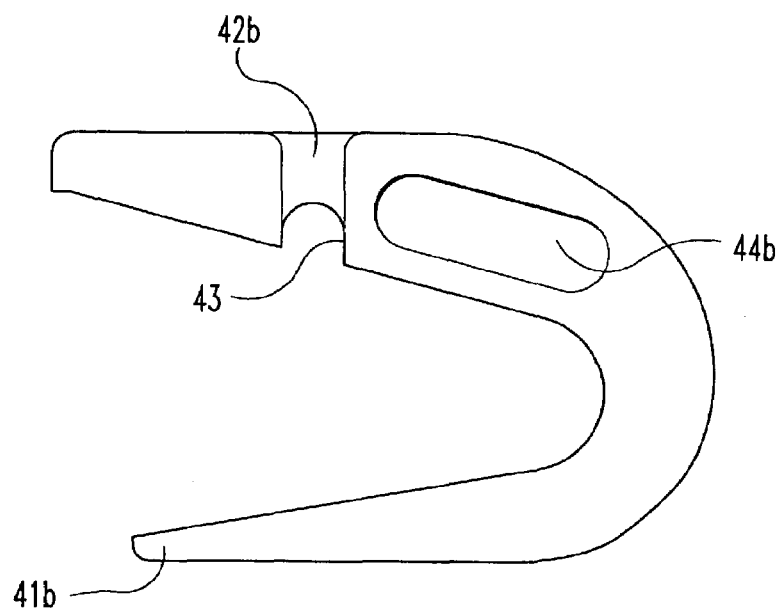
FIG. 9 is a side elevational view of the apparatus of FIG. 6 as taken along line 9-9 of FIG. 6.
Figure 10:
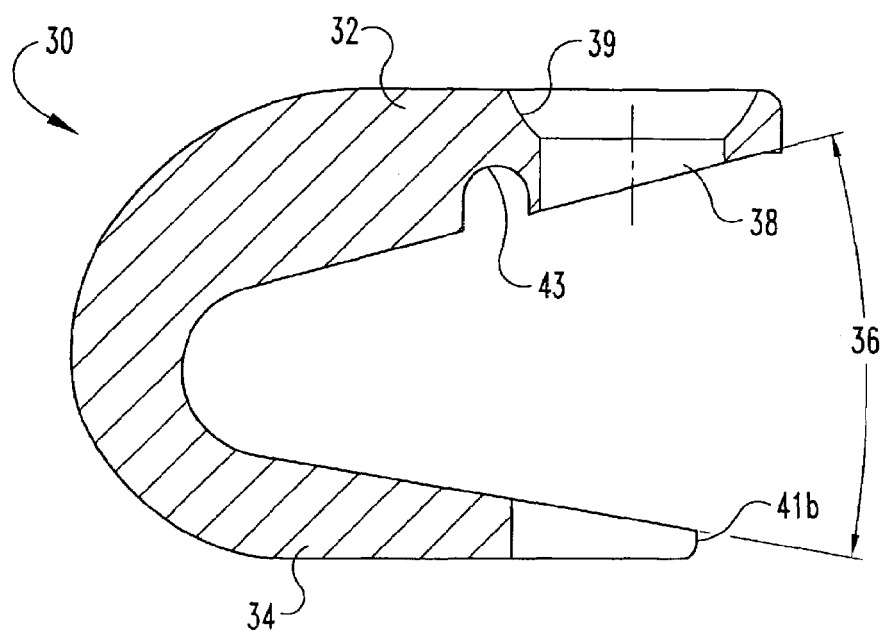
FIG. 10 is a cutaway view of the apparatus of FIG. 6 as taken along line 10-10 of FIG. 6.
Figure 11:
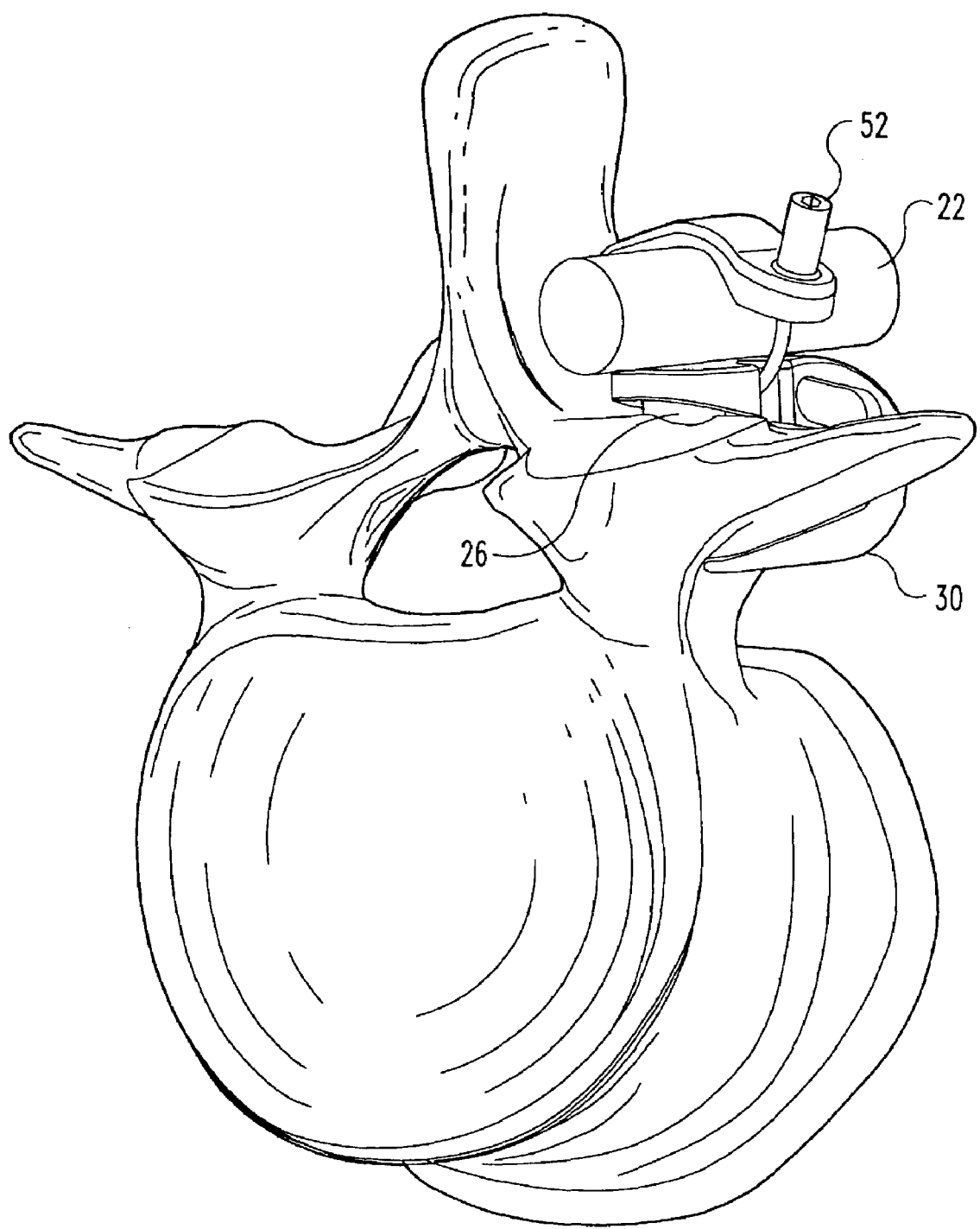
FIG. 11 is a perspective view of the apparatus of FIG. 1 as attached to a vertebrae.
Figure 12:
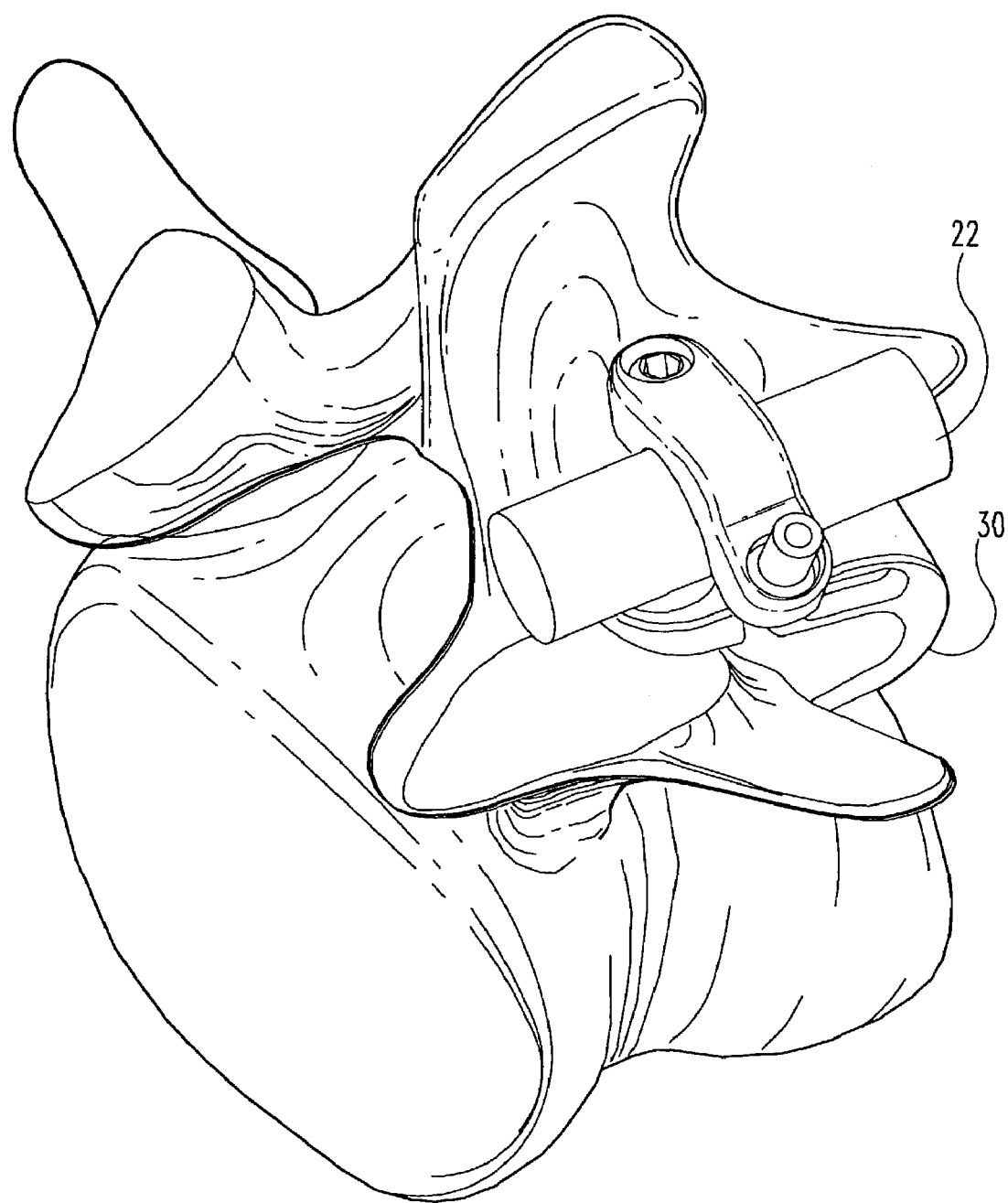
FIG. 12 is a perspective view of the apparatus of FIG. 1 as attached to a vertebrae.
Figure 13:
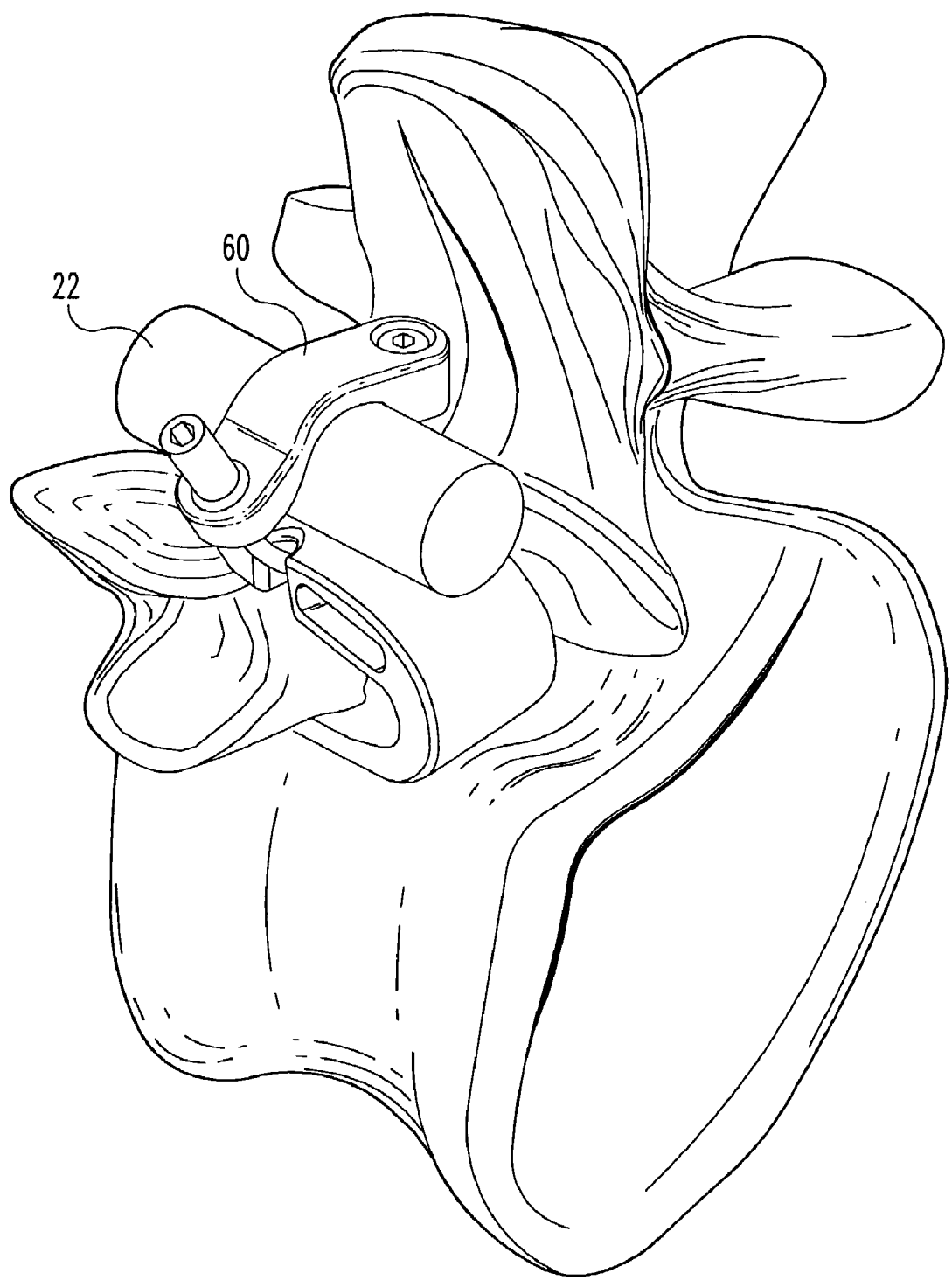
FIG. 13 is a perspective view of the apparatus of FIG. 1 as attached to a vertebrae.
Figure 14:
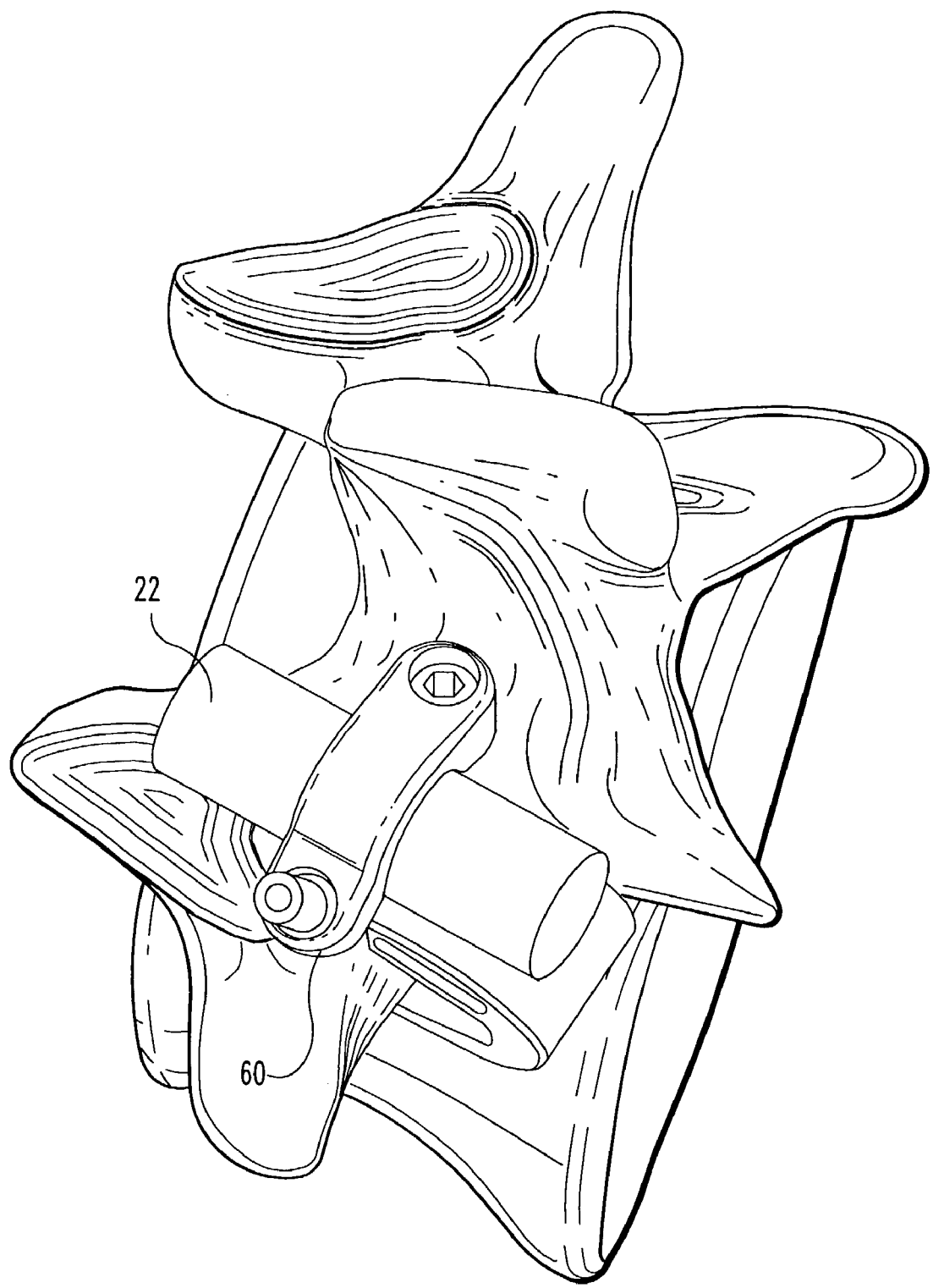
FIG. 14 is a perspective view of the apparatus of FIG. 1 as attached to a vertebrae.

FIGS. 6-10 show various views of a hook-shaped member 30 according to one embodiment of the present invention. Member 30 includes a pair of opposing arms 32 and 34 which are joined at one end and spaced apart at the other end such that member 30 preferably has a "U" or "V" shaped side appearance. Arms 32 and 34 define a groove or pocket 33 therebetween for receiving a portion of bone. In some embodiments, arms 32 and 34 are of different lengths. Referring to FIG. 8, as one example the distance from the topmost outer radius at the joined end of the arms to the bottommost tip of arm 34 is about 14-15 millimeters, whereas the distance from the same outer radius to the bottommost tip of arm 32 is 16 to 17 millimeters. Referring to FIG. 10, in one embodiment the inner, bone-contacting surfaces of arms 32 and 34 are preferably flat and define an included angle 36 of about 20 to 25 degrees. However, the present invention also contemplates those embodiments in which arms 32 and 34 are generally parallel, and also those embodiments in which the included angle is greater than 25 degrees. Preferably, member 30 is fabricated from an alloy such as Ti-6AL-4V according to ASTM F-136. Although reference to specific dimensions and materials are given, the present invention is not limited to such specific details.

Figure 19A:
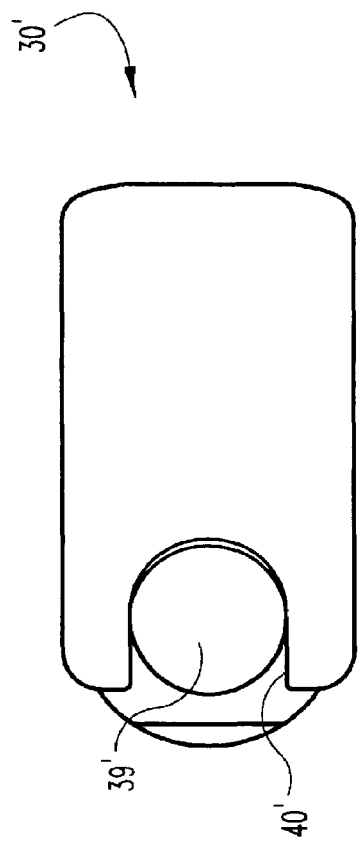
FIG. 19A is a view of the apparatus of FIG. 18 as taken along line 19A-19A of FIG. 18.
Figure 19C:
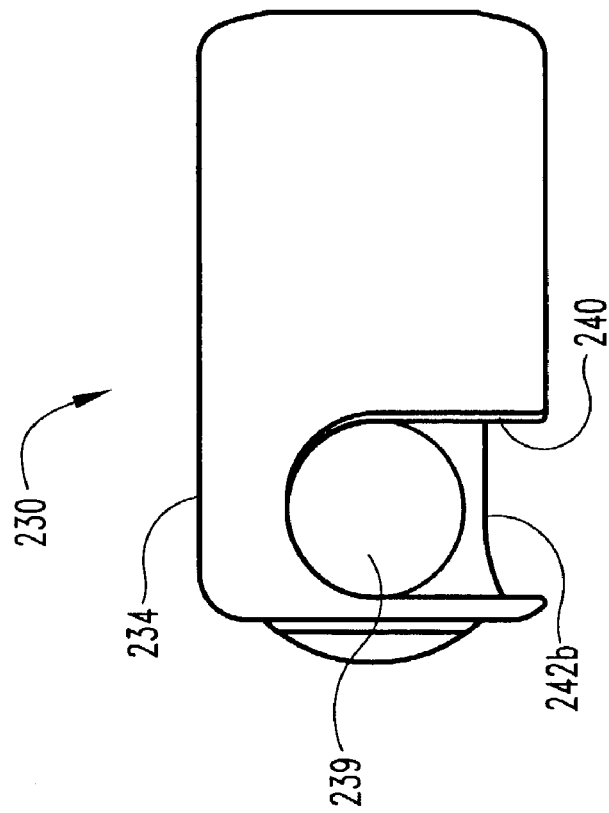
FIG. 19C is a view of a hook-shaped member according to another embodiment of the present invention, as viewed similarly to FIG. 19A.
Figure 19B:
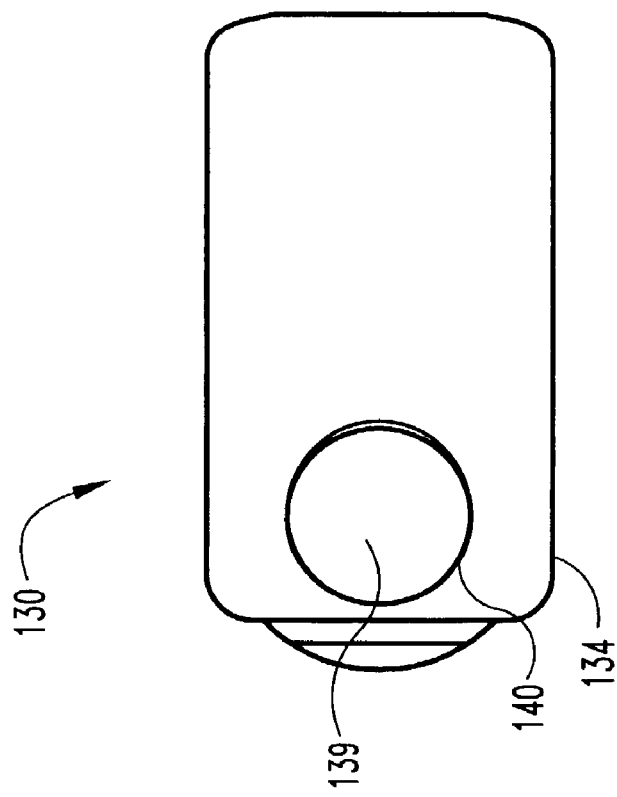
FIG. 19B is a view of a hook-shaped member according to another embodiment of the present invention, as viewed similarly to FIG. 19A.
Figure 21:
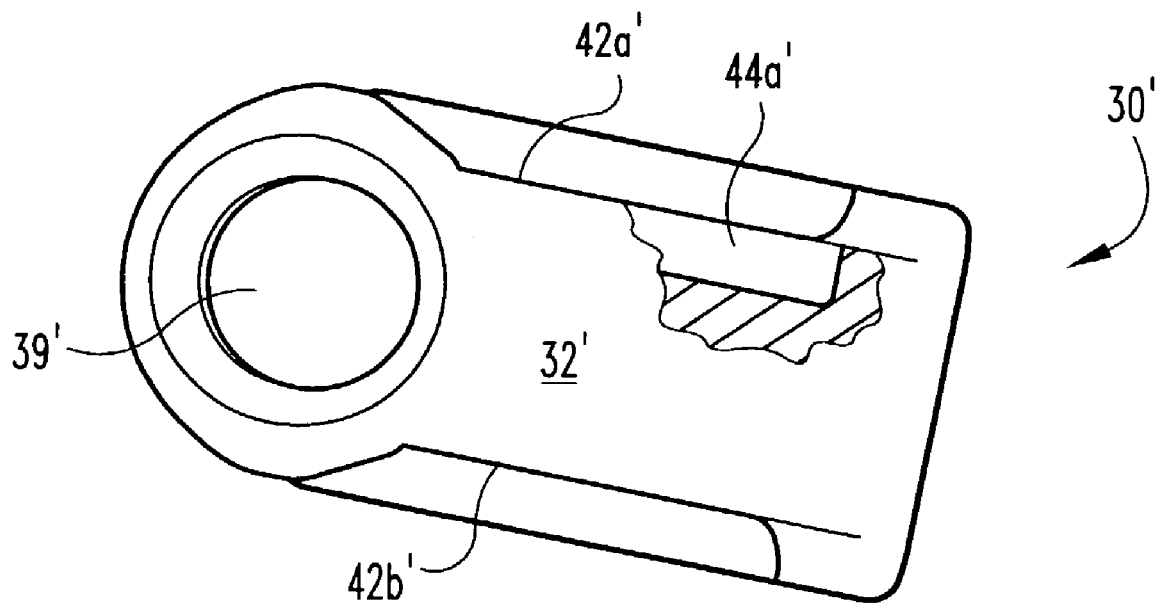
FIG. 21 is a view of the apparatus of FIG. 18 as taken along line 21-21 of FIG. 18.
Figure 22:
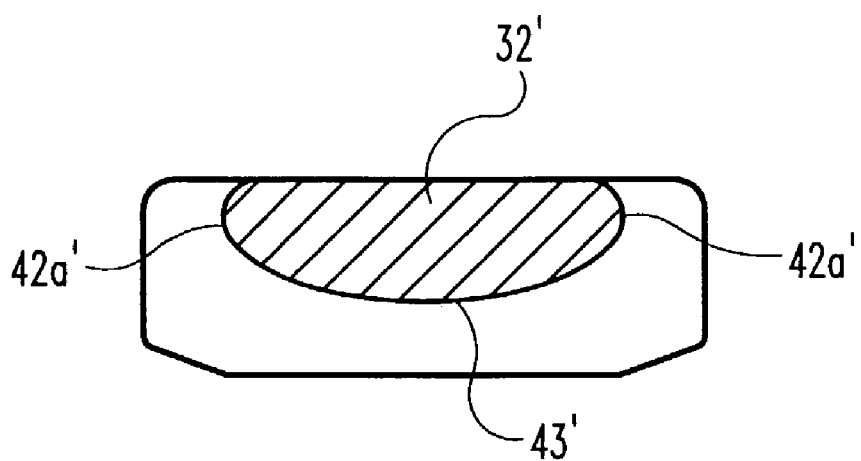
FIG. 22 is a cross sectional view of the apparatus of FIG. 18 as taken along line 22-22 of FIG. 18.

As best seen in FIGS. 7 and 10, arm 32 includes an aperture or through-hole 38 which is sized to accept the shank 27 of screw 26. Arm 32 also includes a radiused pocket 39 which is adapted and configured to permit three-dimensional rotation of surface 28.1 of screw head 28. Referring now to FIGS. 6 and 10, opposing arm 34 includes at its free end a slot 40 located between a pair of extensions 41a and 41b. Extensions 41a and 41b are preferably spaced apart to accept the outer diameter of shank 27, as best seen in FIGS. 1 and 2. However, the present invention also contemplates those embodiments in which the shank of the bone screw passes through an aperture or clearance hole 140 defined by arm 134 of hook 130 (see FIG. 19B). Further, the present invention also contemplates those embodiments in which the arm of a hook 230 includes an aperture or slot 240 to receive the screw shank, except that the slot open end is rotated 90 degrees, such that the open end breaks laterally through a side of arm 34 (an orientation similar to notches 42a and 42b which laterally break through side surfaces of arm 32; see FIG. 19C).

Referring to FIGS. 7, 8, and 9, arm 32 includes a pair of laterally opposing notches 42a and 42b which are sized to accept therein cable 50. A radiused notch 43 extends between notches 42a and 42b. Preferably, notch 43 provides a relief space for cable 50, such that cable 50 does not protrude into the "U" or "V" shaped pocket area 33 and does not contact any bone located therein.

Figure 5:
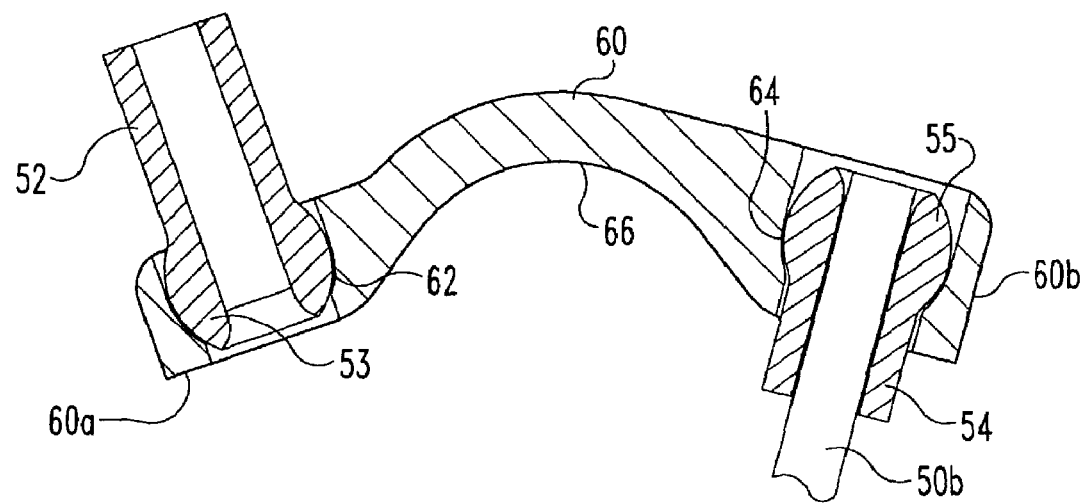
FIG. 5 is an elevational side view of a portion of the assembly of FIG. 1.

Referring now to FIG. 5, a connector 60 provides means for coupling hook member 30 to rod 22. Connector 60 includes a pair of extended portions or opposing ends 60a and 60b which are interconnected by a middle section or rod-coupling portion 66. Portion 66 preferably has a shape that is complementary to the exterior shape of rod 22. In some embodiments of the present invention, the rod has a circular cross sectional shape and middle section 66 includes a complementary semi-circular shape. As best seen in FIG. 2, rod coupling portion 66 has a width or circumferential extent that is about the same as the diameter of rod 22. Rod coupling portion 66 spaces apart opposing ends 60a and 60b such that in some embodiments, the cable does not contact the rod after the cable is tightened. However, the present invention also contemplates those embodiments in which connector 60 is of a geometry such that the cable contacts portions of rod 22.

Each end 60a and 60b preferably includes an internal smooth pocket 62 and 64, respectively. Pockets 62 and 64 rotatably receive fittings 52 and 54, respectively, and permit rotation of the fittings. Fittings 52 and 54 are attached to ends 50a and 50b, respectively, of cable 50. In one embodiment, fitting 54 is a spherical or cable ball end firmly attached to cable end 50b, and fitting 52 is a crimpable cable fitting which is crimped tightly onto cable 50 prior to tightening and cutting cable 50 to the proper length.

FIGS. 11-14 depict various views of an apparatus 20 coupled to a vertebrae. After cutting or otherwise manipulating the vertebrae as required, the surgeon places hook-member 30 proximate to the vertebrae. Member 30 can be held by a forceps with male ends that fit within recesses 44a and 44b. Member 30 is prevented from backing away from the vertebrae by placement of a staple or insertion of screw 26, as shown in FIG. 1. A connector 60 is placed on one side of a spinal rod 22. A length of cable including a fitting 54 is threaded through pocket 64 of connector and threaded around arm 32 of member 30, with the cable being running through 42a, 42b, and 43. The free end of cable 50 is threaded through pocket 62 at the other end of connector 60. A crimpable fitting 52 is placed over the free end of the cable, and moved into proximity with pocket 62. The cable is tightened such that the exterior of rod 22 rests within recess 66, with connector ends 60a and 60b straddling rod 22. After the appropriate tension has been applied, fitting 52 is crimped tightly onto cable 50, and the excess length of cable 50 is removed.

In some embodiments of the present invention, a spinal implant rod has attached to it a plurality of connectors, each connector being coupled by a flexible cable to a plurality of hook-shaped members. In some embodiments, all flexible cables are tightened in order to bring each hook-shaped member into contact with the rod. In yet other embodiments, the flexible cables are tightened such that none of the hook-shaped members are in contact with the rod. It is appreciated that in yet other embodiments, some of the cables are tightened to place one or more of the hooks in contact with the rod, and other cables are tightened such that one or more of the hooks are spaced apart from the rod.

FIGS. 15-25 depict hook-shaped members according to various alternate embodiments of the present invention. The use of a prime (') designation refers to an element that is the same as the non-prime element, except for those differences shown or described. The use of an "N" prefix (NXX) refers to an element that is the same as the non-prefixed element (XX), except for those differences shown or described.

Figure 20:
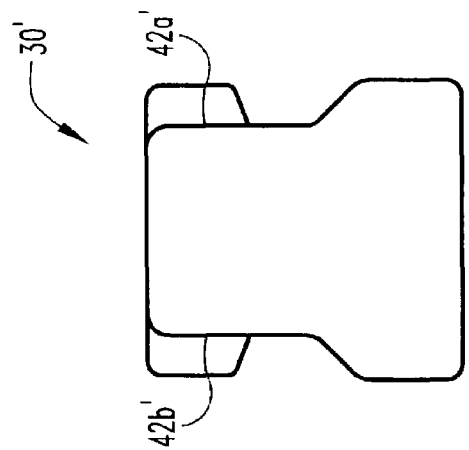
FIG. 20 is a view of the apparatus of FIG. 18 as taken along line 20-20 of FIG. 18.
Figure 18:
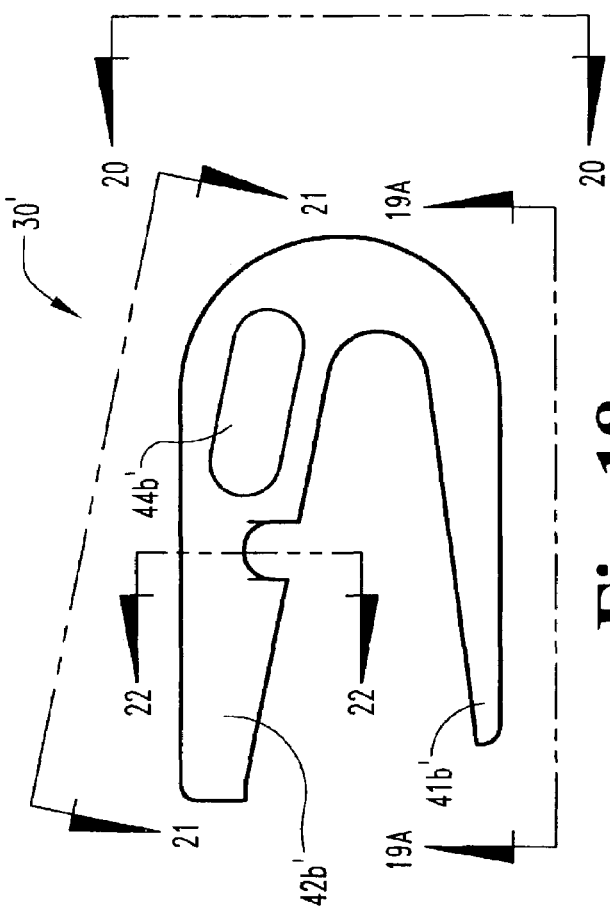
FIG. 18 is a view of the apparatus of FIG. 15 as taken along line 18-18 of FIG. 15.

As best seen in FIGS. 15, 16, and 20, hook-shaped member 30' includes reduced-width portions 42a' and 42b' along laterally opposing sides of arm 34'. As seen best in FIG. 16, these reduced-width portions 42a' and 42b' blend into larger-width portions both at the juncture of arms 34' and 32', and also in the vicinity of aperture 38'. These reduced-width portions coact with slot 43' both to accurately locate the cable, and also to minimize sharp bends in the cable.

Figure 23:
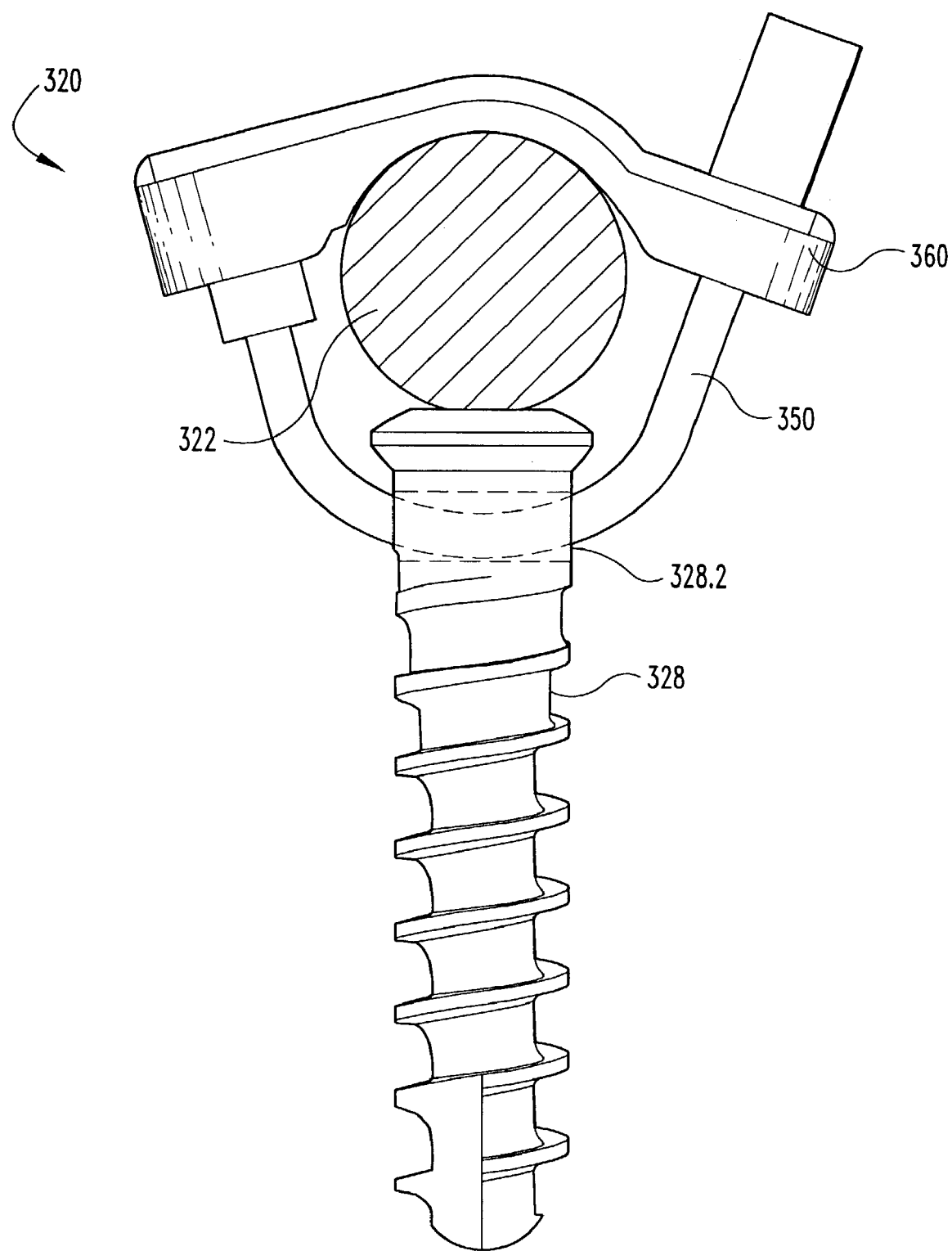
FIG. 23 is a side elevational view according to another embodiment of the present invention.

FIG. 23 is a side elevational view according to another embodiment of the present invention. Apparatus 320 is the same as apparatus 20, except for the changes shown and described. Apparatus 320 eliminates the hook-shaped member from the assembly. Instead, anchor 328 defines an aperture or through hole 328.2 that passes through the anchor. Cable 350 and connector 360 coact to couple rod 322 to anchor 328. In some embodiments, head 329 may include a cylindrical recess to accept the exterior shape of rod 322.

Figure 24:
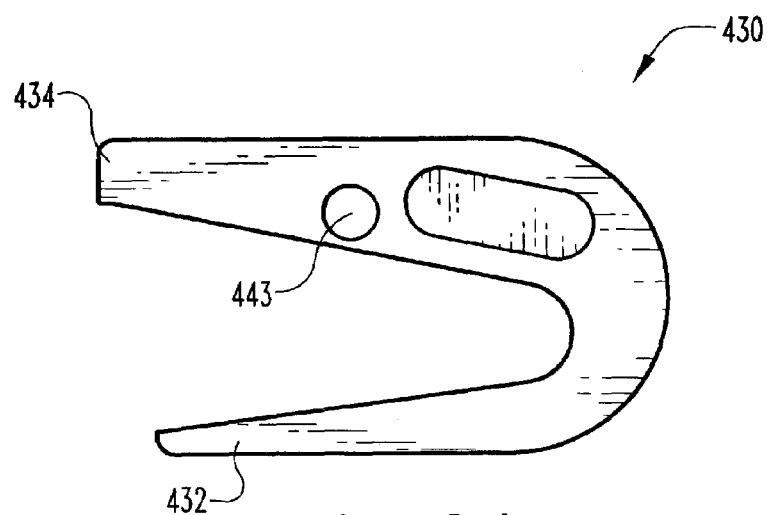
FIG. 24 is a side elevational view of an apparatus according to another embodiment of the present invention.

FIG. 24 is a side elevational view of a hook-shaped member 430 according to another embodiment of the present invention. Member 430 includes a slot 443 that is open on either end and enclosed therebetween. Cable 450 (not shown) passes through slot 443.

Figure 25:
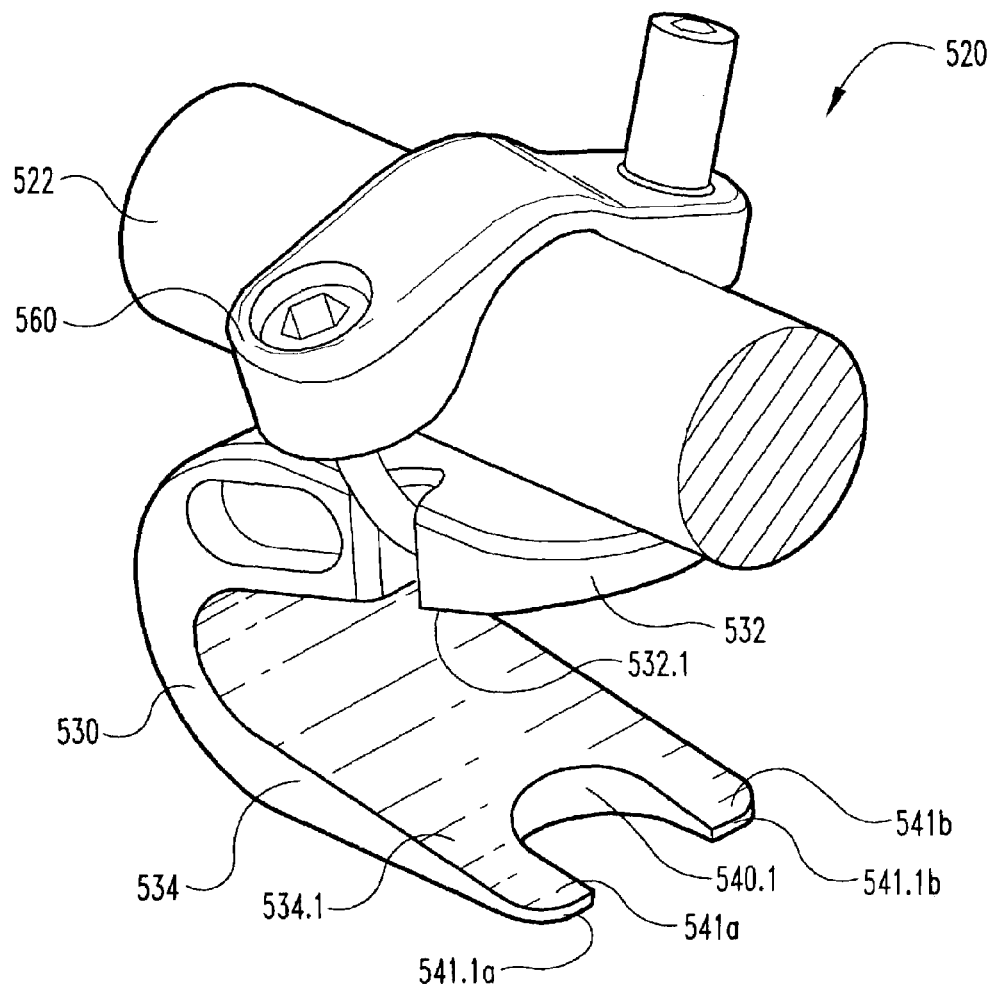
FIG. 25 is a perspective view of a cable and hook member assembly according to another embodiment of the present invention.

FIG. 25 is a perspective view of an assembly 520 according to another embodiment of the present invention. Alignment apparatus 520 is the same as apparatus 20, except that the bone anchor is omitted. In some embodiments, hook-shaped member 530 may include any of the barbs, prongs, tines, or pointed tips as disclosed in U.S. Pat. No. 6,299,613, issued Oct. 9, 2001 to Ogilvie et al. These barbs, prongs, tines, and/or pointed tips (not shown) may be included on one or more of the inner surface 534.1 of arm 534, the inner surface 532.1 of arm 532, the end surfaces 541.1a and 541.1b of extensions 541a and 541b, respectively; and/or the inner wall 540.1 of aperture 540.

This application incorporates by reference U.S. Pat. No. 5,569,253 to Farris and Bonner, issued Oct. 29, 1996; and also U.S. Pat. No. 5,782,831 to Sherman and Drewry, issued Jul. 21, 1998, and also U.S. Pat. No. 6,299,631 to Ogilvie et al, issued Oct. 9, 2001.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An apparatus for alignment of vertebrae, comprising:
   a surgical rod;
   a hook-shaped member including first and second arms connected at one end and spaced apart at the other end to form a pocket therebetween for receiving a portion of bone, one of said arms defining an open slot;
   a bone anchor coupling said book-shaped member to a bone;
   a cable coupling said hook-shaped member to said rod and having first and second ends, a portion of said cable being received within the open slot; and
   a connecting member having a first extended portion connected to the first end of said cable and a second extended portion connected to the second end of said cable and a middle section between the first extended portion and the second extended portion, wherein the middle section spaces apart said first and second extended portions such that said cable does not contact said rod after tightening.

2. The apparatus of claim 1 wherein the other of said arms defines an aperture and a portion of said bone anchor passes through the aperture.

3. The apparatus of claim 1 wherein the one of said arms defines an aperture and a portion of said bone anchor passes through the aperture.

4. The apparatus of claim 1, wherein said slot is configured to provide a relief space so that said cable does not touch any bone within said pocket of said hook-shaped member.

5. An apparatus for alignment of vertebrae, comprising:
   a surgical rod;

a bone anchor having an upper portion and a lower portion adapted and configured for fixation to a bone, said upper portion defining an aperture therethrough;

a cable coupling said bone anchor to said rod and having first and second ends, a portion of said cable passing through the aperture; and a connecting member having a first extended portion connected to the first end of said cable and a second extended portion connected to the second end of said cable and a middle section between the first extended portion and the second extended portion, wherein the middle section spaces apart said first and second extended portions such that said cable does not contact said rod after tightening.

6. The apparatus of claim 5, wherein said bone anchor includes a hook.

7. The apparatus of claim 6, wherein said bone anchor includes a screw inserted through a portion of said hook.

8. The apparatus of claim 6, wherein said hook has a first side surface and a second side surface, and said aperture includes a slot extending from said first side surface to said second side surface.

9. The apparatus of claim 6 wherein said hook has a first side surface and a second side surface, and said aperture is at least one notch in at least one of said side surfaces.

10. The apparatus of claim 5, wherein said bone anchor includes a screw.

11. The apparatus of claim 10, wherein said aperture extends through said screw.

12. The apparatus of claim 10, wherein said cable is offset from said screw.

13. The apparatus of claim 5, wherein said connecting member includes a first pocket in said first extended portion for receiving the first end of said cable and a second pocket in said second extended portion for receiving the second end of said cable.

14. The apparatus of claim 5, wherein said middle section of said connecting member has a configuration generally complementary to the cross-section of said rod.

15. The apparatus of claim 5, wherein at least one of the ends of said cable include a spherical portion.

16. The apparatus of claim 5, wherein at least one of the ends of said cable includes a crimpable fitting.

17. An orthopedic medical apparatus, comprising:
a surgical rod;
a hook-shaped member adapted and configured for receiving a portion of bone within the hook, said member defining an aperture therethrough;
an anchor having a body adapted and configured for fixation into a bone and a head, said body passing through the aperture when fixed to the bone;
a cable coupling said hook-shaped member to said rod wherein said cable has first and second ends;
and a connecting member defining a first pocket for receiving therein the first end of said cable and a second pocket for receiving therein the second end of said cable, and a middle section between the first pocket and the second pocket for contacting said rod; and
wherein said connecting member is non-unitary with said hook-shaped member.

18. The apparatus of claim 17, wherein said middle section of said connecting member has a configuration generally complementary to the cross-section of said rod.

19. The apparatus of claim 17, wherein at least one of the ends of said cable includes a spherical portion.

20. The apparatus of claim 17, wherein at least one of the ends of said cable includes a crimpable fitting.

21. The apparatus of claim 17, wherein said hook-shaped member has a first side surface and a second side surface, at least one of said side surfaces including a notch for receiving said cable.

22. An orthopedic medical apparatus, comprising:
a surgical rod;
a hook-shaped member adapted and configured for receiving a portion of bone within the hook;
a cable coupling said hook-shaped member to said rod and having first and second ends, one of said first and second ends of said cable including a spherical portion;
a connecting member defining a first pocket for receiving therein the one end, said first pocket including a spherical recess adapted and configured for receiving therein the spherical end portion of the one end; and
wherein said connecting member is non-unitary with said hook-shaped member.

23. The apparatus of claim 22, wherein said middle section of said connecting member has a configuration generally complementary to the cross-section of said rod.

24. The apparatus of claim 22, wherein at least one of the ends of said cable includes a spherical portion.

25. The apparatus of claim 22, wherein at least one of the ends of said cable includes a crimpable fitting.

26. The apparatus of claim 22, wherein said hook-shaped member has a first side surface and a second side surface, at least one of said side surfaces including a notch for receiving said cable.

27. An orthopedic medical apparatus, comprising:
a surgical rod having a first cross-sectional shape;
a hook-shaped member adapted and configured for receiving a portion, of bone within the hook;
a cable coupling said hook-shaped member to said rod and having first and second ends;
a connecting member having a first extended portion connected to the first end of said cable and a second extended portion connected to the second end of said cable, and having a middle section between the first and second extended portions; and
wherein said rod is clamped between said connecting member and said hook-shaped member.

28. The apparatus of claim 27, wherein said middle section of said connecting member has a configuration generally complementary to the cross-section of said rod.

29. The apparatus of claim 27, wherein at least one of the ends of said cable include a spherical portion.

30. The apparatus of claim 27, wherein at least one of the ends of said cable includes a crimpable fitting.

31. The apparatus of claim 27, wherein said hook-shaped member has a first side surface and a second side surface, at least one of said side surfaces including a notch for receiving said cable.

32. An apparatus for alignment of vertebrae, comprising:
a hook member having an upper branch, a lower branch, and a space between said branches for receiving a portion of bone, said upper branch having a lower surface abutting said space and an opposite upper surface;
a surgical rod, a portion of said rod contacting said upper surface of said hook member;
a connector having a first end, a second end, and a medial portion, said first end having a first hole and said second end having a second hole, wherein said connector contacts a part of said rod generally opposite to said rod portion contacting said upper surface of said hook member;

a cable having a first end, a second end, and a middle portion between said cable ends, said first end of said cable being within said first hole, said second end of said cable extending into or through said second hole, said ends of said cable being separated so that said cable does not contact itself, said middle portion of said cable extending around and contacting a portion of said upper branch of said hook member.

33. The apparatus of claim 32, further comprising a bone screw extending through at least one of said upper branch and said lower branch.

34. The apparatus of claim 33, wherein said rod covers at least a portion of said bone screw.

35. The apparatus of claim 32, wherein said medial portion has a configuration generally complementary to the cross-section of said rod.

36. The apparatus of claim 32, wherein at least one of the ends of said cable includes a spherical portion.

37. The apparatus of claim 32, wherein at least one of the ends of said cable includes a crimpable fitting.

38. The apparatus of claim 32, wherein said hook-shaped member has a first side surface and a second side surface, at least one of said side surfaces including a notch for receiving said cable.

* * * * *